US012661508B2

(12) United States Patent
Lee et al.

(10) Patent No.: US 12,661,508 B2
(45) Date of Patent: Jun. 23, 2026

(54) BRAIN STIMULATION DEVICE AND BRAIN STIMULATION SYSTEM

(71) Applicant: KT&G CORPORATION, Daejeon (KR)

(72) Inventors: Won Kyeong Lee, Gyeonggi-do (KR); Min Kyu Kim, Seoul (KR); Paul Joon Sunwoo, Seoul (KR)

(73) Assignee: KT&G Corporation, Daejeon (KR)

( * ) Notice: Subject to any disclaimer, the term of this patent is extended or adjusted under 35 U.S.C. 154(b) by 265 days.

(21) Appl. No.: 18/562,065

(22) PCT Filed: Jun. 2, 2023

(86) PCT No.: PCT/KR2023/007623
§ 371 (c)(1),
(2) Date: Nov. 17, 2023

(87) PCT Pub. No.: WO2023/234744
PCT Pub. Date: Dec. 7, 2023

(65) Prior Publication Data
US 2025/0082934 A1 Mar. 13, 2025

(30) Foreign Application Priority Data

Jun. 2, 2022 (KR) ........................ 10-2022-0067694
Aug. 9, 2022 (KR) ........................ 10-2022-0099428

(51) Int. Cl.
*A61N 1/36* (2006.01)
*A61N 1/04* (2006.01)
(52) U.S. Cl.
CPC ....... *A61N 1/36031* (2017.08); *A61N 1/0456* (2013.01); *A61N 1/36034* (2017.08)

(58) Field of Classification Search
CPC ............ A61N 1/36031; A61N 1/36034; A61N 1/0456
(Continued)

(56) References Cited

U.S. PATENT DOCUMENTS 9,648,907 B2 5/2017 Kobal et al.
2007/0006889 A1 1/2007 Kobal et al.
(Continued)

FOREIGN PATENT DOCUMENTS

EP 3 968 164 A1 3/2022
JP 6856704 B2 4/2021
(Continued)

OTHER PUBLICATIONS

International Search Report for PCT/KR2023/007623, dated Sep. 8, 2023.
(Continued)

*Primary Examiner* — Nadia A Mahmood
(74) *Attorney, Agent, or Firm* — Foley & Lardner LLP

(57) ABSTRACT

A brain stimulation system includes a wearable electronic device including a display, a biometric information acquisition unit, and a first processor, and a brain stimulation device having at least one area that is attached to the body of a user and configured to apply brain stimulation to the user such that the user feels a smoking sensation. The biometric information acquisition unit detects changed biometric information of the user in response to the brain stimulation, and the first processor displays one of a virtual reality image and an augmented reality image including the detected biometric information of the user on the display.

15 Claims, 10 Drawing Sheets

(58) Field of Classification Search
USPC .......................................................... 607/62
See application file for complete search history.

(56)                References Cited

U.S. PATENT DOCUMENTS

| | | |
|---|---|---|
| 2020/0249762 A1 | 8/2020 | Keller et al. |
| 2021/0011545 A1 | 1/2021 | Min |
| 2021/0223864 A1* | 7/2021 | Forsland ................. G06F 3/147 |
| 2022/0248772 A1 | 8/2022 | Kim et al. |

FOREIGN PATENT DOCUMENTS

| | | | | |
|---|---|---|---|---|
| KR | 10-2008-0014742 A | 2/2008 | | |
| KR | 1020190108727 A | 9/2019 | | |
| KR | 10-2021-0042754 A | 4/2021 | | |
| KR | 10-2021-0153329 A | 12/2021 | | |
| KR | 20210153329 A | * 12/2021 | ............. | A24F 40/50 |
| WO | 2018/139820 A1 | 8/2018 | | |

OTHER PUBLICATIONS

Written Opinion for PCT/KR2023/007623, dated Sep. 8, 2023.
Extended European Search Report dated Sep. 23, 2024, received in
European Patent Application No. 23809437.9.

\* cited by examiner

[Fig. 1]
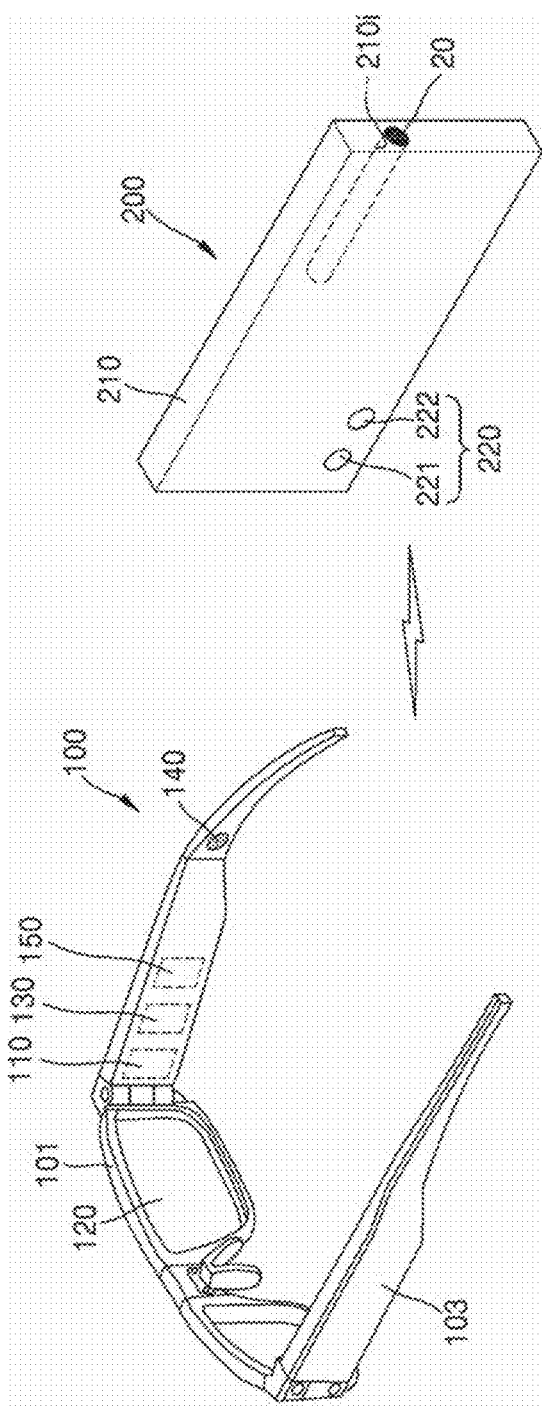

[Fig. 2]
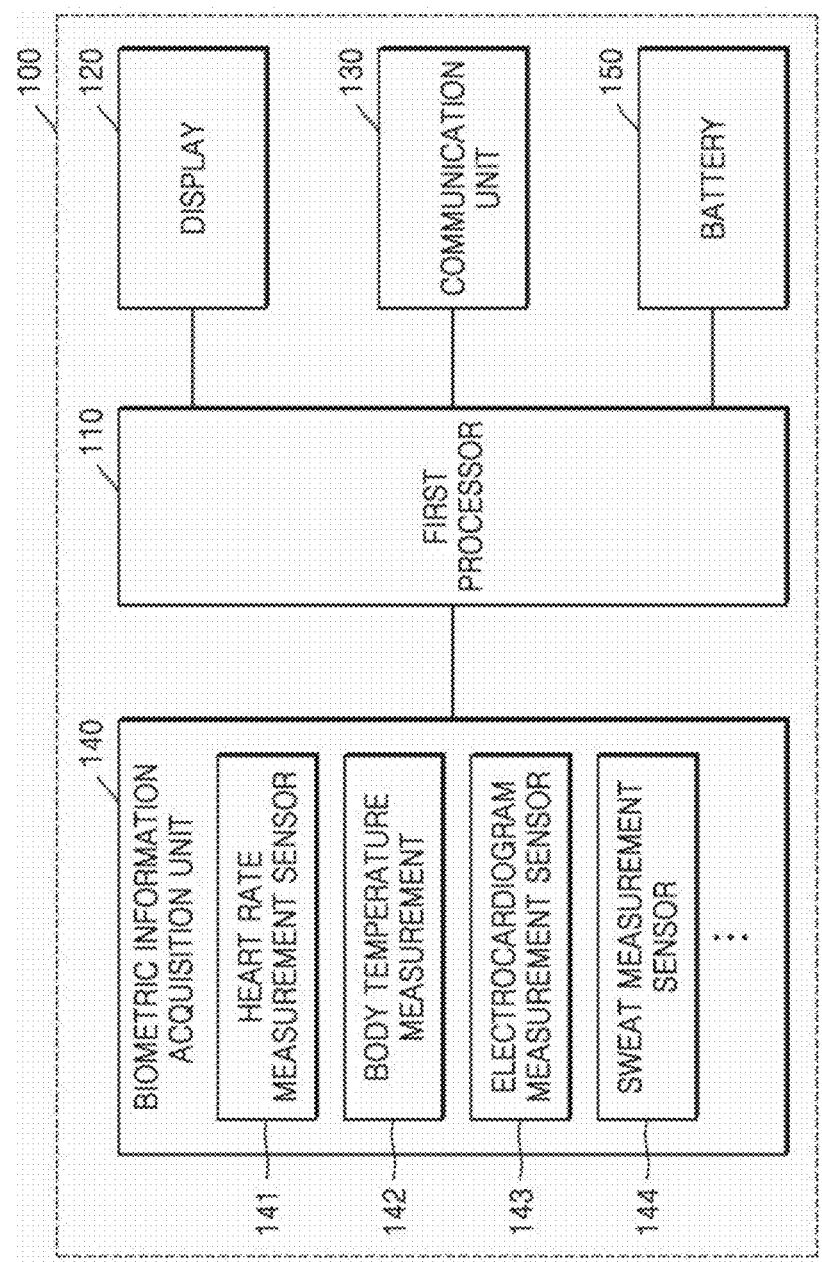

[Fig. 3]
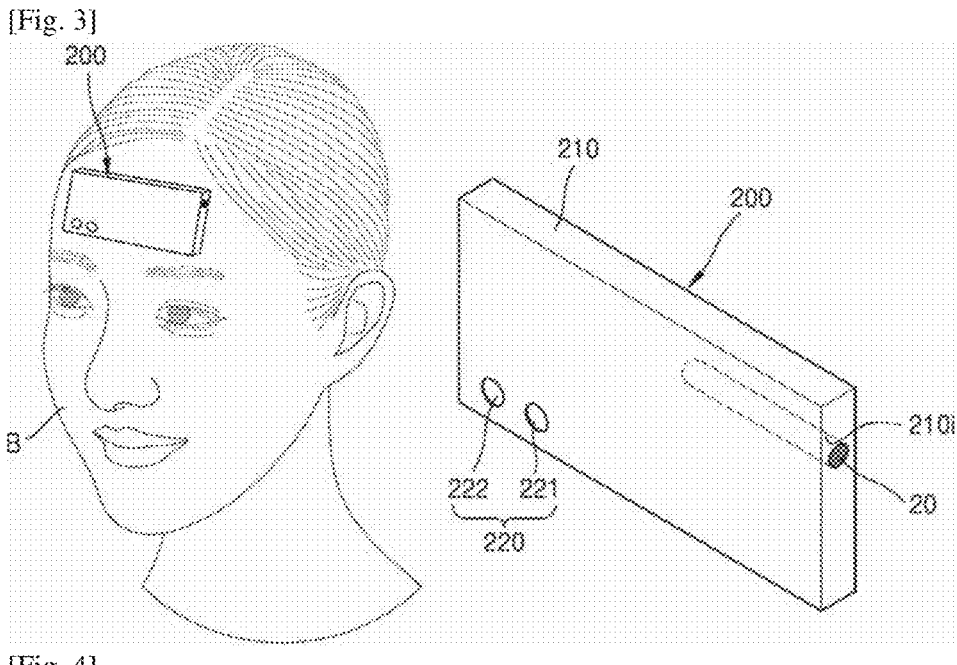
[Fig. 4]
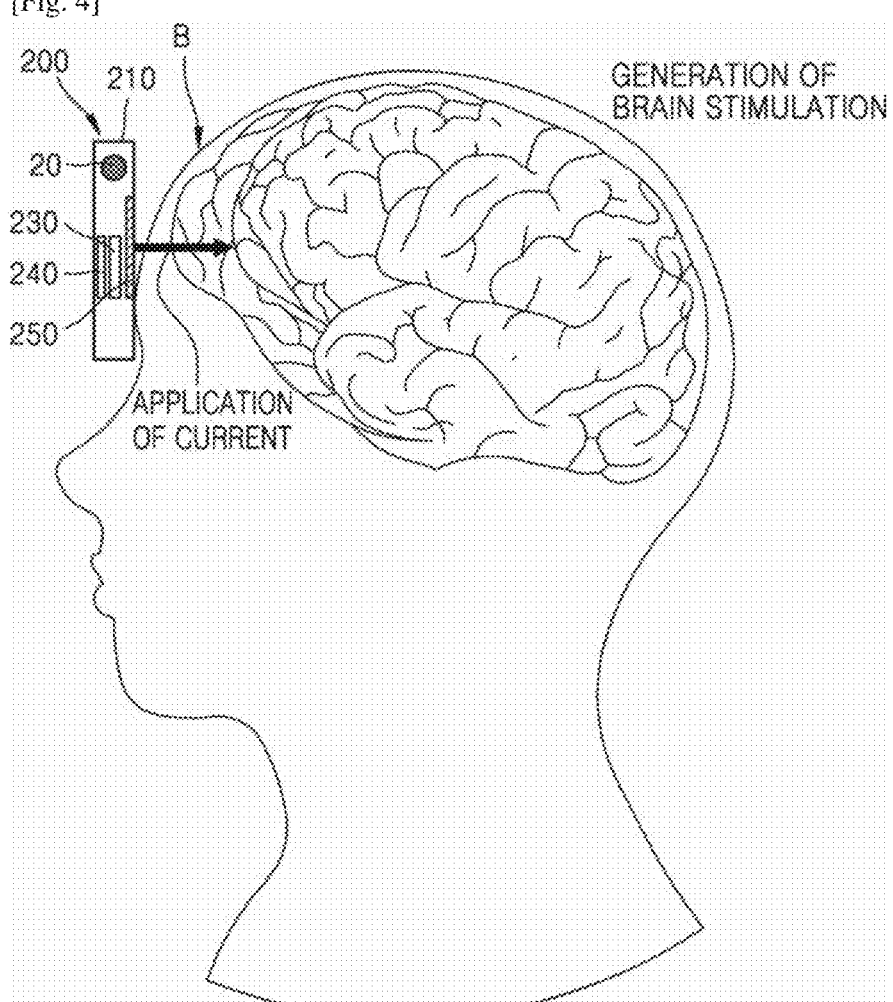

[Fig. 5]
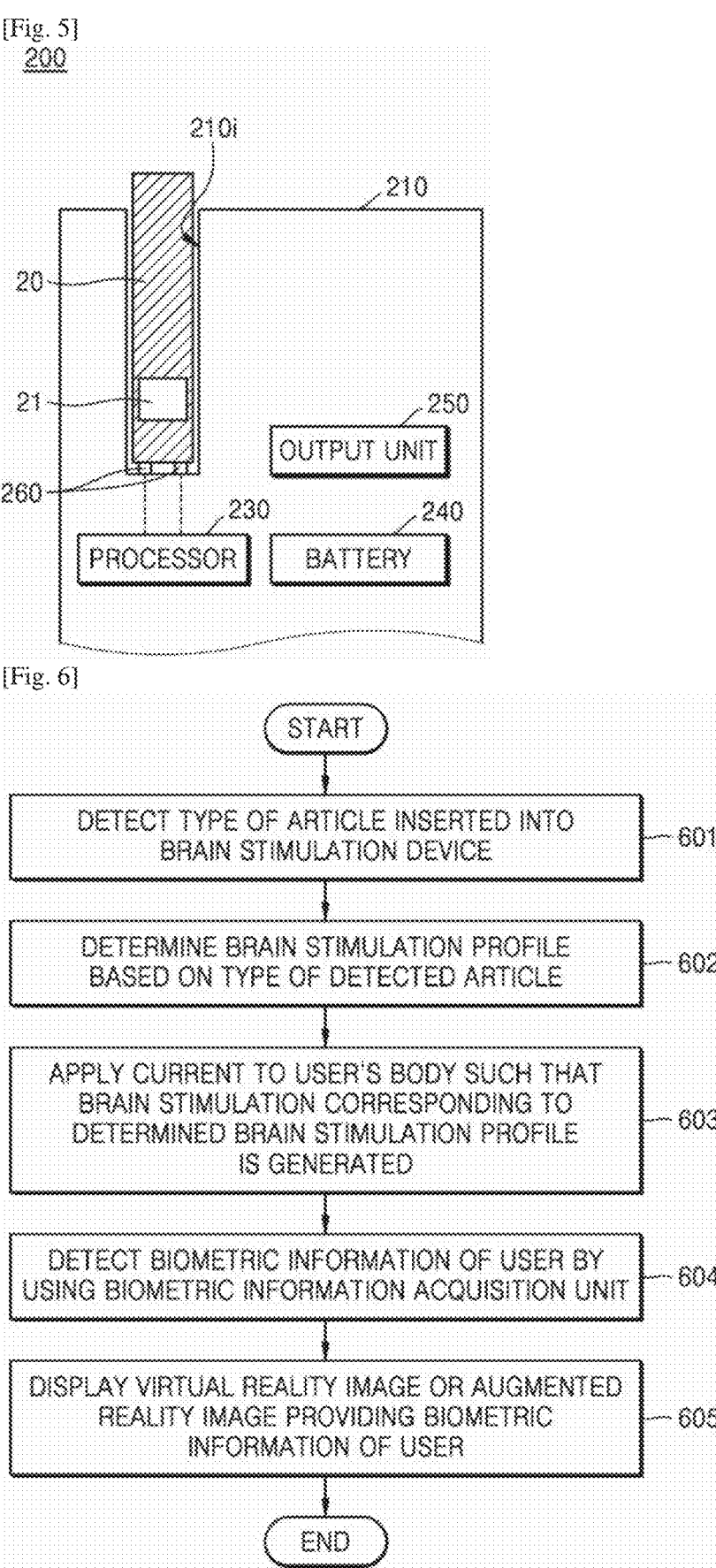
[Fig. 6]

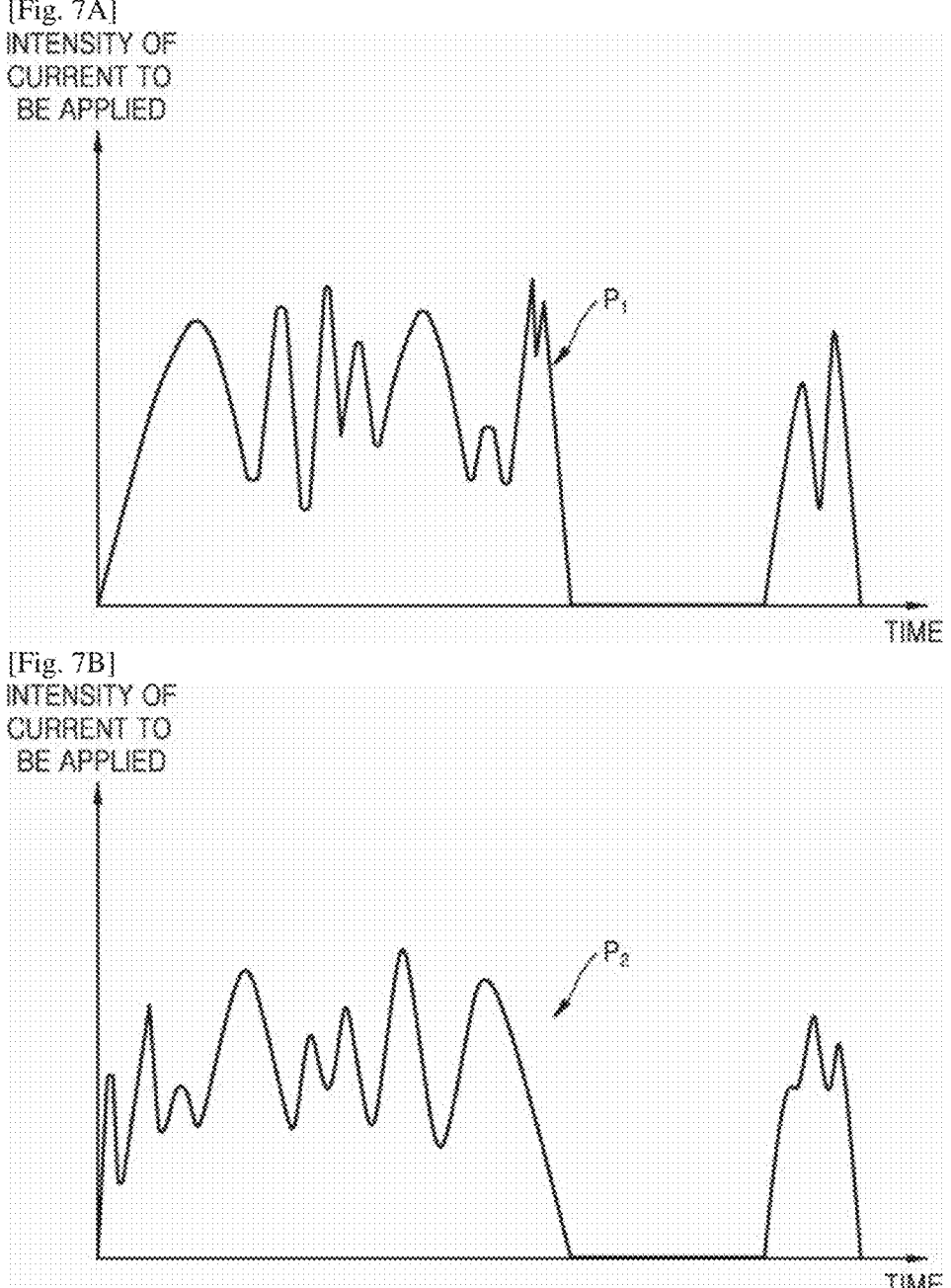
[Fig. 7A]
INTENSITY OF
CURRENT TO
BE APPLIED
TIME
[Fig. 7B]
INTENSITY OF
CURRENT TO
BE APPLIED
TIME

[Fig. 8A]
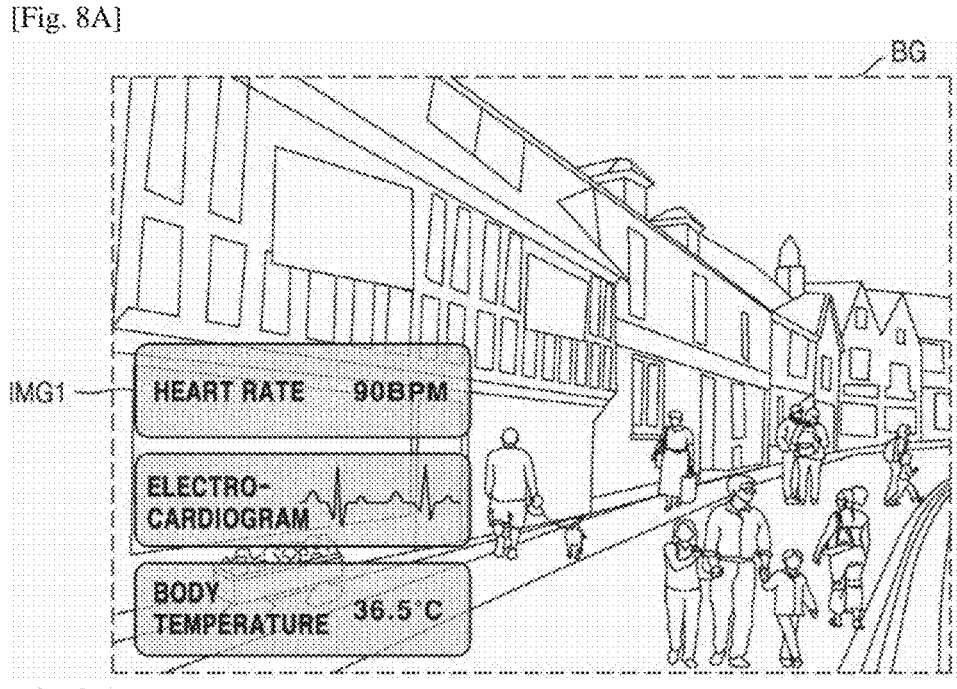
[Fig. 8B]
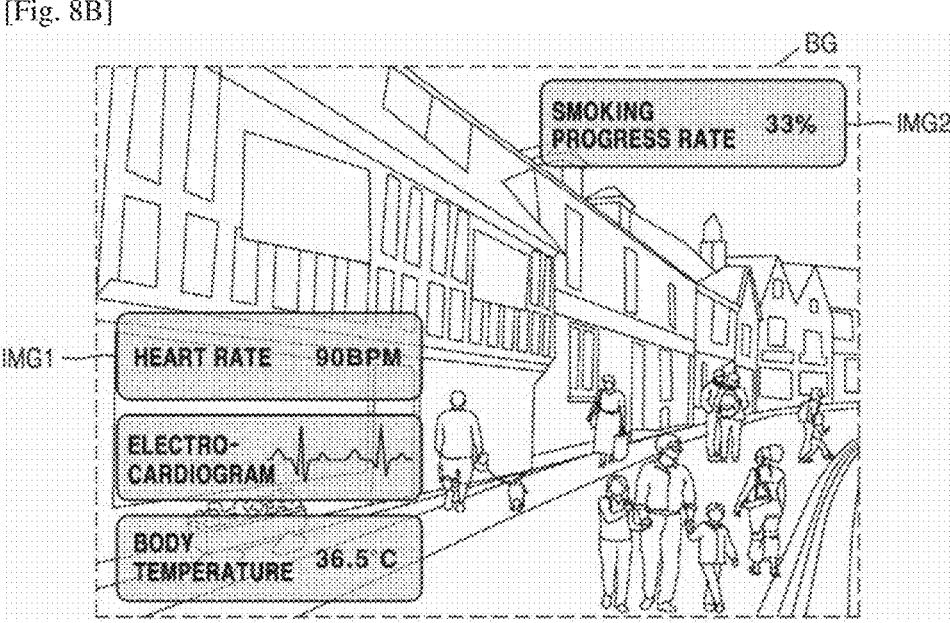

[Fig. 8C]
[Fig. 9A]
[Fig. 9B]
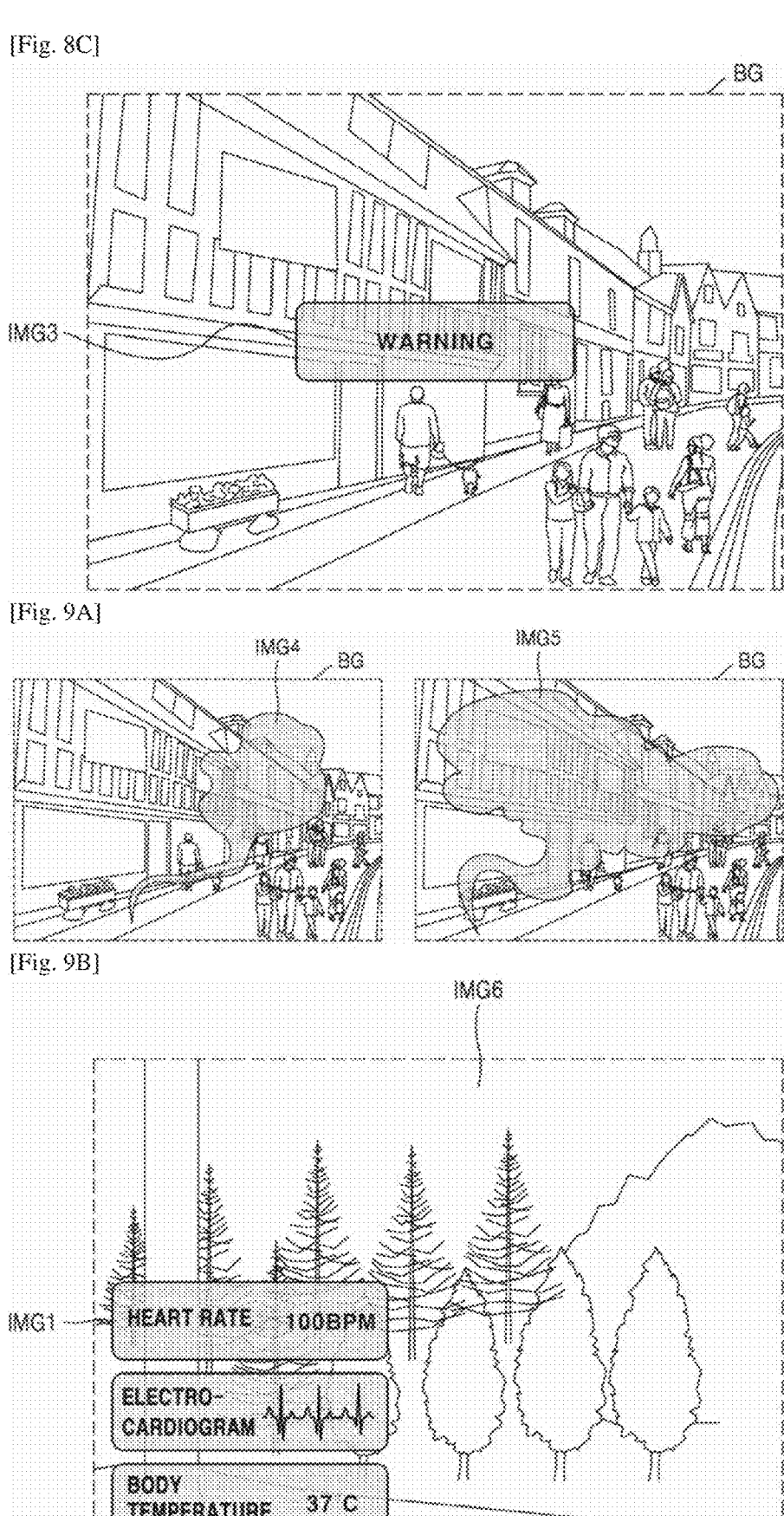

[Fig. 9C]
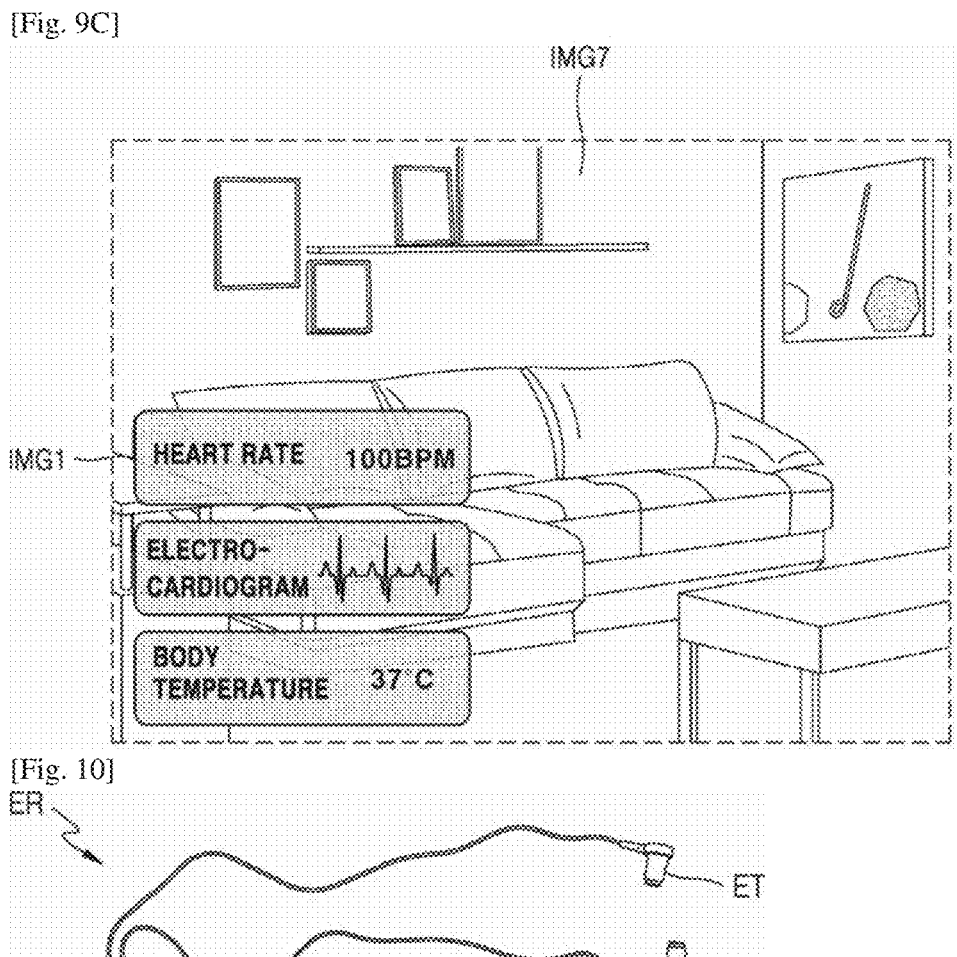
[Fig. 10]

[Fig. 11]
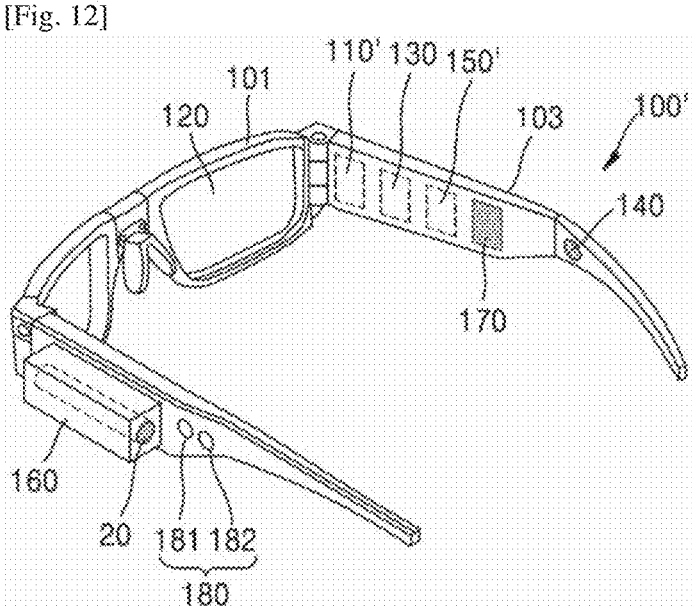
[Fig. 12]

[Fig. 13]
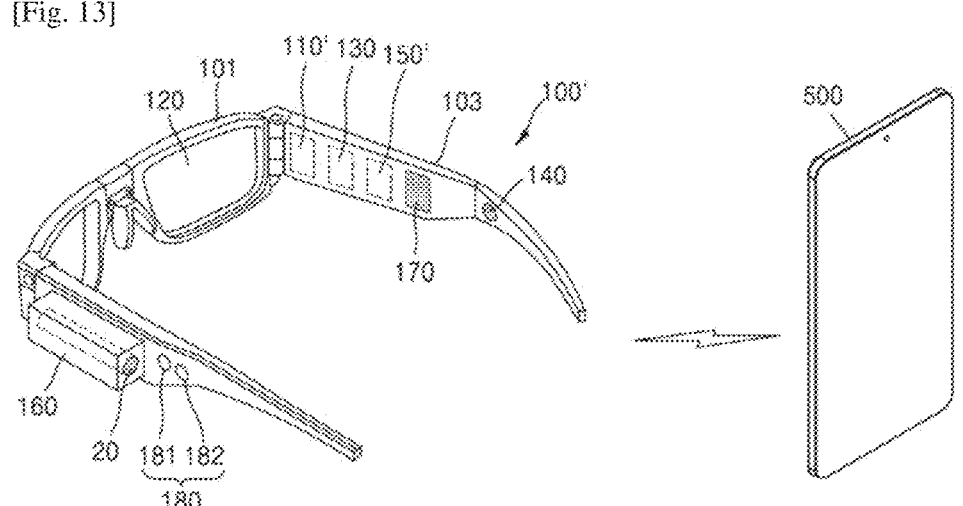

BRAIN STIMULATION DEVICE AND BRAIN STIMULATION SYSTEM

This application is a National Stage of International Application No. PCT/KR2023/007623 filed Jun. 2, 2023, claiming priority based on Korean Patent Application No. 10-2022-0067694 filed Jun. 2, 2022 and Korean Patent Application No. 10-2022-0099428 filed Aug. 9, 2022.

TECHNICAL FIELD

Various embodiments relate to a brain stimulation device and a brain stimulation system including the same, and more particularly, to a brain stimulation device and a brain stimulation system that may provide a smoking effect to a user through brain stimulation without inhalation.

BACKGROUND ART

With the development of molecular biology, evolutionary biology, electro-physiology, bioinformatics, and so on, research on brain science, which analyzes complex functions and structures of the brain and studies methods for activating various functions of the brain, is gradually increasing.

As the research on the brain science progresses, development of brain stimulation devices for treating diseases by applying electrical stimulation to nerves has increased. For example, the brain stimulation devices may apply electrical stimulation to a user's nerves by applying a micro-current to the body after being attached to the user's body (for example, the forehead).

The brain stimulation devices have been mainly used for treatment of diseases, such as depression and dementia, or for stress relief of users. However, as development of brain stimulation devices progresses, attempts to use nerve stimulation devices are gradually increasing in various fields including disease treatment or stress relief.

When a user's brainwaves before and after smoking are measured and analyzed, and electrical stimulation corresponding to the brainwaves changed due to smoking is applied to the user, the user may feel a smoking sensation without a separate smoking behavior.

DISCLOSURE OF INVENTION

Technical Problem

An object of the present disclosure is to improve reliability according to use of a brain stimulation device and a brain stimulation system.

An object of the present disclosure is to improve an effect of stress relief when a brain stimulation device and a brain stimulation system are used.

Objects to be achieved through the embodiments are not limited to the objects described above, and objects not described may be clearly understood by those skilled in the art to which the embodiments belong from the present specification and the accompanying drawings.

Solution to Problem

A brain stimulation system according to one embodiment includes a wearable electronic device including a display, a biometric information acquisition unit, and a first processor, and a brain stimulation device having at least one area that is attached to the body of a user and configured to apply brain stimulation to the user such that the user feels a smoking sensation. The biometric information acquisition unit detects biometric information of the user that changes in response to the brain stimulation, and the first processor displays one of a virtual reality image and an augmented reality image including the detected biometric information of the user on the display.

A brain stimulation device according to one embodiment includes a display, a biometric information acquisition unit, an accommodation space in which an article is accommodated, an output unit having at least one area that is attached to the body of a user and configured to apply a current corresponding to the article to the body of the user to apply brain stimulation to the user such that the user feels a smoking sensation, and a processor configured to control operations of the display, the biometric information acquisition unit, and the output unit. The biometric information acquisition unit detects biometric information of the user that changes in response to the brain stimulation, and the processor displays one of a virtual reality image and an augmented reality image including the detected biometric information of the user on the display.

Advantageous Effects of Invention

A brain stimulation device and a brain stimulation system according to the disclosed embodiments may display biometric information of a user which is detected by a sensor on a display, and thus, reliability according to use may be improved.

A brain stimulation device and a brain stimulation system according to the disclosed embodiments may display a virtual reality image or an augmented reality image for assisting a smoking effect on a display, and thus, an effect of stress relief may be improved.

Effects of the embodiments are not limited to the effects described above, and effects not described will be clearly understood by those skilled in the art to which the embodiments belong from the present specification and the accompanying drawings.

BRIEF DESCRIPTION OF DRAWINGS

FIG. 1 illustrates a schematic view of a brain stimulation system according to one embodiment.

FIG. 2 illustrates a schematic block diagram of a wearable electronic device according to one embodiment.

FIG. 3 is a perspective view of a brain stimulation device according to one embodiment.

FIG. 4 is a view illustrating a process in which the brain stimulation device of FIG. 3 applies a current to a user's body.

FIG. 5 is a cross-sectional view illustrating an electrical connection between the brain stimulation device of FIG. 3 and an article accommodated in the brain stimulation device.

FIG. 6 is a flowchart illustrating operations of a brain stimulation system.

FIG. 7A is a graph illustrating an example of a change in current applied to a user's body when a first article is inserted into a brain stimulation device.

FIG. 7B is a graph illustrating an example of a change in current applied to a user's body when a second article is inserted into a brain stimulation device.

FIG. 8A is a view illustrating that detected biometric information of a user is displayed as a virtual reality image or an augmented reality image.

FIG. 8B is a view illustrating that a smoking progress rate is displayed as a virtual reality image or an augmented reality image.

FIG. 8C is a view illustrating that a use stop warning message to stop use is displayed as a virtual reality image or an augmented reality image.

FIG. 9A is a view illustrating that cigarette smoke is displayed as a virtual reality image or an augmented reality image.

FIGS. 9B and 9C are views illustrating that a natural environment or a certain space for stress relief is displayed as a virtual reality image.

FIG. 10 is a view illustrating a sound reproduction device according to one embodiment.

FIG. 11 is a perspective view illustrating a brain stimulation device according to another embodiment.

FIG. 12 illustrates a schematic view of a brain stimulation device according to one embodiment.

FIG. 13 is a perspective view illustrating the brain stimulation device illustrated in FIG. 12 and an external electronic device.

MODE FOR THE INVENTION

Regarding the terms in the various embodiments, the general terms which are currently and widely used are selected in consideration of functions of structural elements in the various embodiments of the present disclosure. However, meanings of the terms can be changed according to intention, a judicial precedence, the appearance of a new technology, and the like. In addition, in certain cases, terms which can be arbitrarily selected by the applicant in particular cases. In such a case, the meaning of the terms will be described in detail at the corresponding portion in the description of the present disclosure. Therefore, the terms used in the various embodiments of the present disclosure should be defined based on the meanings of the terms and the descriptions provided herein.

In addition, unless explicitly described to the contrary, the word "comprise" and variations such as "comprises" or "comprising" will be understood to imply the inclusion of stated elements but not the exclusion of any other elements. In addition, the terms "-er", "-or", and "module" described in the specification mean units for processing at least one function and operation and can be implemented by hardware components or software components and combinations thereof.

Hereinafter, embodiments of the present disclosure will be described in detail with reference to the accompanying drawings such that those skilled in the art to which the present disclosure belongs may easily implement the present disclosure. However, the present disclosure may be implemented in many different forms and is not limited to the embodiments described herein.

Hereinafter, embodiments of the present disclosure will be described in detail with reference to the drawings.

FIG. 1 illustrates a schematic view of a brain stimulation system according to one embodiment.

Referring to FIG. 1, a brain stimulation system 1 may include a wearable electronic device 100 and a brain stimulation device 200. In the present disclosure, the wearable electronic device 100 may indicate an electronic device wearable by a user. For example, the wearable electronic device 100 may correspond to a wearable head mounted display (HMD) (for example, augmented reality (AR) glass, a virtual reality (VR) device, or so on) in the form of glasses or goggles.

In the present disclosure, the brain stimulation device 200 may refer to a device that has at least one area attached to a user's body and applies electrical stimulation corresponding to brain waves changed by smoking to a user to apply brain stimulation to the user such that the user may feel a smoking sensation without a separate smoking behavior. For example, the brain stimulation device 200 may include a housing 210 having a rectangular patch shape that may be attached to a user's forehead, an accommodation space 210i formed in the housing 210 to accommodate an article 20, and a button portion 220 including a first button portion 221 for controlling electric power and a second button portion 222 for controlling a current. In addition, an article of the same shape as a known aerosol generating article may be inserted into (or detached from) the brain stimulation device 200. In this case, the article is a memory stick. For example, as shown in FIG. 3, the article may have a shape similar to a cigarette. However, it is obvious to those skilled in the art that a shape of the article is not limited thereto and may be changed depending on designs of a manufacturer.

In one embodiment, the wearable electronic device 100 may include a face plate 101 and a mounting portion 103.

In one embodiment, the face plate 101 of the wearable electronic device 100 may be worn on at least a part of a front surface of a user's face. For example, the face plate 101 may include various components (for example, a nose pad) that may be supported by at least a part of the front surface of the user's face (for example, the bridge of the nose).

In one embodiment, the mounting portion 103 of the wearable electronic device 100 may be coupled to a part of the face plate 101 and supported by a part (for example, an ear) of the user's body. For example, the mounting portion 103 may be composed of a temple, a strap, or a helmet such that the face plate 101 may come into close contact with a periphery of the user's eye.

In one embodiment, the wearable electronic device 100 may include a first processor 110, a display 120, a communication unit 130, a biometric information acquisition unit 140, and a first battery 150. In one embodiment, although the first processor 110, the communication unit 130, the biometric information acquisition unit 140, and the first battery 150 may be in at least one part of the mounting portion 103 of the wearable electronic device 100, the portion where the first processor 110, the communication unit 130, the biometric information acquisition unit 140, and the first battery 150 are arranged is not limited thereto. In another embodiment, at least one of the first processor 110, the communication unit 130, the biometric information acquisition unit 140, and the first battery 150 may be in one portion of the face plate 101 of the wearable electronic device 100, other than the display 120. In one embodiment, the display 120 may be in the form of a lens of eyeglasses, and accordingly, the display 120 may be in the face plate 101 of the wearable electronic device 100.

In one embodiment, the wearable electronic device 100 may communicate with the brain stimulation device 200 through a communication interface. For example, the communication unit 130 of the wearable electronic device 100 may communicate with the brain stimulation device 200 by being connected to a network through wireless or wired communication. The wireless communication may include at least one of wireless fidelity (WI-FI), Bluetooth (BT), near field communication (NFC), or cellular communication (for example, LTE, LTE-A, CDMA, WCDMA, UMTS, and so on). The wired communication may include at least one of a universal serial bus (USB) and a high definition multimedia interface (HDMI).

In one embodiment, the wearable electronic device 100 may output a variety of image data onto the display 120 based on data received from the brain stimulation device 200 through the communication unit 130 and biometric information detected by the biometric information acquisition unit 140. Details on this will be described below.

FIG. 2 illustrates a schematic block diagram of a wearable electronic device according to one embodiment.

Referring to FIGS. 1 and 2, the wearable electronic device 100 may include the first processor 110, the display 120, the communication unit 130, the biometric information acquisition unit 140, and the first battery 150.

The first processor 110 may control all operations of the wearable electronic device 100. For example, the first processor 110 may be implemented as an array of a plurality of logic gates or may be implemented as a combination of a general-purpose microprocessor and a memory in which programs executable by the microprocessor are stored. In addition, those skilled in the art to which the present embodiment belongs may understand that the first processor may be implemented as other types of hardware. A detailed operation of the first processor 110 will be described below with reference to FIG. 6 and FIGS. 8A to 9C.

The display 120 may be controlled to be transparent or opaque depending on the purpose of use. When the wearable electronic device 100 provides a virtual reality image, the display 120 may be controlled to be opaque, and when the wearable electronic device 100 provides an augmented reality image, the display 120 may be controlled to be transparent. For example, the display 120 may be made of plastic, such as polycarbonate or a glass material but is not limited thereto. In addition, at least one of light reflection and anti-glare coating, anti-fog coating, and ultraviolet blocking coating may be applied to the display 120.

The display 120 may visually provide information on the wearable electronic device 100 to a user. For example, the information on the wearable electronic device 100 may indicate charging/discharging state information of the first battery 150 of the wearable electronic device 100.

The communication unit 130 may be at least one of a wireless LAN (Wi-Fi), Bluetooth, ZigBee, Wi-Fi Direct (WFD), ultra wideband (UWB), infrared data association (IrDA), Bluetooth low energy (BLE), near field communication (NFC), and Ant+, but the communication method is not limited thereto.

The biometric information acquisition unit 140 may detect biometric information of a user wearing the wearable electronic device 100 and transmit the detected biometric information to the first processor 110.

In one embodiment, the biometric information acquisition unit 140 may include a heart rate measurement sensor 141. For example, the heart rate measurement sensor 141 may detect contraction or expansion of a blood vessel based on reflection of light that changes according to a change in blood volume in the blood vessel of the skin of a user's body. The first processor 110 may receive an electrical signal from the heart rate measurement sensor 141 and calculate a heart rate.

In one embodiment, the biometric information acquisition unit 140 may include a body temperature measurement sensor 142. For example, the body temperature measurement sensor 142 may include an infrared body temperature sensor to measure temperature by measuring the amount of infrared generated from a skin surface of a user.

In one embodiment, the biometric information acquisition unit 140 may include an electrocardiogram (ECG) measurement sensor 143. For example, the electrocardiogram measurement sensor 143 may include a plurality of electrodes that may come into contact with a user's skin to measure an electrocardiogram pattern of a user.

In one embodiment, the biometric information acquisition unit 140 may include a sweat measurement sensor 144. For example, the sweat measurement sensor 144 may be composed of an ion sensor and may detect ions included in sweat of a user in real time to measure an ion concentration pattern.

Although not illustrated in FIG. 2, the biometric information acquisition unit 140 according to one embodiment may include an oxygen saturation measurement sensor, a blood glucose measurement sensor, and a blood pressure measurement sensor. In this case, the biometric information acquisition unit 140 may measure the degree of oxygen saturation, blood glucose, and blood pressure when the brain is stimulated by the brain stimulation device 200.

The first battery 150 may supply power used to operate the wearable electronic device 100. The first battery 150 may be a rechargeable battery or a disposable battery. For example, the first battery 150 may be a lithium polymer (LiPoly) battery but is not limited thereto.

FIG. 3 is a perspective view of a brain stimulation device according to one embodiment.

Referring to FIG. 3, the brain stimulation device 200 according to one embodiment may include at least one area attached to a user's body B and apply a current to the user's body B to apply brain stimulation to the user such that the user may feel a smoking sensation.

In the present disclosure, the "smoking sensation" may indicate sensation that a user may feel through smoking, and a brain stimulation device may provide the user with brain stimulation corresponding to brain stimulation applied by smoking such that the user feels the smoking sensation. In this case, the brain stimulation device of the present disclosure may be referred to as a "brain stimulation device for smoking" but is not limited thereto.

According to one embodiment, the brain stimulation device 200 may include the housing 210 to which at least one area is attached to the user's body B, and at least one button portion 220 that receives a user input.

The housing 210 may form the entire appearance of the brain stimulation device 200 and include the accommodation space 210i for accommodating the article 20. At least a part of the article 20 may be inserted into or accommodated in the accommodation space 210i, and the brain stimulation device 200 may detect the type of the article 20 inserted into the accommodation space 210i and control the brain stimulation applied to a user based on the type of the detected article 20. However, detailed descriptions thereof will be described below.

In one example, the housing 210 may be formed in a rectangular patch shape as a whole, but the shape of the housing 210 is not limited thereto. In another example, the housing 210 may be formed in an elliptical patch shape or a polygonal patch shape.

In addition, the housing 210 may be attached to a user's forehead as illustrated in FIG. 3, but the user's body B to which the housing 210 is attached is not limited to the illustrated embodiment. In another example, the housing 210 may be attached to a user's cheek or neck.

At least one button portion 220 may be on an outer surface of the housing 210 to receive a user input. A processor (not illustrated) of the brain stimulation device 200 may control operation of the brain stimulation device 200 based on the user input to at least one button portion 220.

According to one embodiment, at least one button portion 220 may include the first button portion 221 for controlling a power state of the brain stimulation device 200 and the second button portion 222 for controlling the intensity of brain stimulation applied to a user. However, the number of at least one button portion 220 is not limited to the above-described embodiment, and the number of button portions may increase or decrease depending on embodiments.

In one example, when receiving a user input to the first button portion 221, a processor of the brain stimulation device 200 may change a power state of the brain stimulation device 200 from an on-state to an off-state or change the power state from an off-state to an on-state.

In another example, when receiving a user input to the second button portion 222, the processor of the brain stimulation device 200 may control the intensity of brain stimulation applied to the user by adjusting the intensity of a current applied to the user.

For example, the processor may adjust the intensity of a current applied to a user such that strong brain stimulation is applied to the user or brain stimulation is rapidly applied to the user, based on the user input to the second button portion 222. In another example, the processor may adjust the intensity of a current applied to a user such that relatively weak brain stimulation Is applied to the user or brain stimulation is slowly applied to the user, based on the user input to the second button portion 222.

In addition, the processor may adjust a frequency of a current applied to a user to adjust the intensity of brain stimulation applied to the user or the time when the brain stimulation is applied, based on the user input to the second button portion 222.

Hereinafter, a configuration for applying a current to a user's body that uses the brain stimulation device 200 will be described in detail with reference to FIG. 4.

FIG. 4 is a diagram illustrating a process in which brain stimulation device of FIG. 3 applies a current to a user's body.

Referring to FIG. 4, the brain stimulation device 200 according to one embodiment may include the housing 210, a second processor 230, a second battery 240, and an output unit 250. At least one of components of the brain stimulation device 200 according to one embodiment may be the same as or similar to at least one of the components of the brain stimulation device (for example, the brain stimulation device 200 of FIG. 3) of FIG. 3, and redundant descriptions thereof are omitted below.

The housing 210 may include an accommodation space (for example, the accommodation space 210*i* of FIG. 3) in which the article 20 may be accommodated, or an internal space (or a 'mounting space) in which components of the brain stimulation device 200 may be arranged. For example, the second processor 230, the second battery 240, and the output unit 250 may be in an inner space of the housing 210 but are not limited thereto.

The second processor 230 may control overall operations of the brain stimulation device 200. For example, the second processor 230 may be implemented as an array of a plurality of logic gates or may be implemented as a combination of a general-purpose microprocessor and a memory in which programs executable by the microprocessor are stored. In addition, those skilled in the art to which the present embodiment belongs may understand that the second processor may be implemented in other types of hardware.

According to one embodiment, the second processor 230 may detect the type of the article 20 accommodated in or inserted into the housing 210 and control a current applied to the user's body B from the output unit 250. In the present disclosure, the expression of 'controlling a current applied to the user's body B from the output unit 250' means that the intensity and/or frequency of a current applied to the user's body B from the output unit 250 may be controlled, and the expression may be used in the same meaning below.

For example, when it is detected that a first article is accommodated in the housing 210, the second processor 230 may control the output unit 250 such that a current corresponding to a first current profile is applied to the user's body B. In another example, when it is detected that a second article different from the first article is accommodated in the housing 210, the second processor 230 may control the output unit 250 such that a current corresponding to a second current profile different from the first current profile is applied to the user's body B. In the present disclosure, the "current profile" may indicate a change in current over time, and the expression may be used in the same meaning below.

The second processor 230 may apply brain stimulation to a user such that the user may feel a smoking sensation by applying a current to the user's body B through the output unit 250. Accordingly, a user may feel a smoking sensation through the brain stimulation applied by the brain stimulation device 200 without a separate smoking behavior, and a detailed description of the control operation of the second processor 230 for the output unit 250 will be described below.

The second battery 240 may supply power used for the brain stimulation device 200 to operate. In one example, the second battery 240 may supply power required to operate the second processor 230. In another example, the second battery 240 may supply power required for the output unit 250 to apply a current to the user's body B. The second battery 240 may be a rechargeable battery or a disposable battery. For example, the second battery 240 may be a lithium polymer (LiPoly) battery, but the type of the second battery 240 is not limited thereto.

The output unit 250 may generate stimulation to a user's brain by applying a current to the user's body B through power supplied from the second battery 240. That is, the output unit 250 may provide brain stimulation to a user by using the power supplied from the second battery 240.

For example, the output unit 250 may include at least one electrode (not illustrated) generating a micro-current through the power supplied from the second battery 240. At least one area of the output unit 250 may come into contact with the user's body B, and a micro-current generated by at least one electrode may be applied to the user's body B through one area of the output unit 250 that comes into contact with the user's body B. As the micro-current generated by the output unit 250 is applied to a user's brain circuit, stimulation may occur in the user's brain. In this case, the output unit 250 may apply a micro-current to the user's body B such that brain stimulation corresponding to the brain stimulation generated by smoking is applied to the user, and as a result, a user may feel a smoking sensation without a smoking behavior.

According to one embodiment, the second processor 230 may detect the type of the article 20 accommodated in or inserted into the housing 210 and the intensity or frequency of a current applied to the user's body B from the output unit 250 based on the type of the detected article 20. As a result, the second processor 230 may provide various types of brain stimulation to a user depending on the type of the article 20. Hereinafter, a process in which the second processor 230 detects the type of the article 20 to be accommodated in or inserted into the housing 210 will be described in detail with reference to FIG. 5.

FIG. 5 is a cross-sectional view illustrating an electrical connection between the brain stimulation device of FIG. 3 and an article accommodated in the brain stimulation device.

Referring to FIG. 5, a brain stimulation device 200 according to one embodiment may include a housing 210, a second processor 230, a second battery 240, an output unit 250, and at least one electrical connection member 260. At least one of components of the brain stimulation device 200 according to one embodiment may be the same as or similar to at least one of the components of the brain stimulation device (for example, the brain stimulation device 200 of FIG. 3 or 4) of FIGS. 3 and 4, and redundant descriptions thereof are omitted below.

The at least one electrical connection member 260 may be in the accommodation space 210*i* of the housing 210 and may come into contact with the article 20 when the article 20 is accommodated in or inserted into the accommodation space 210*i*. For example, when the article 20 is accommodated in or inserted into the accommodation space 210*i*, the at least one electrical connection member 260 may come into contact with the article 20 to be electrically connected with a memory 21 embedded in the article 20.

For example, the at least one electrical connection member 260 may include a pogo-pin, but the type of at least one electrical connection member 260 is not limited thereto. In another example, the at least one electrical connection member 260 may include at least one electrode or a flexible printed circuit board (FPCB).

In the present disclosure, the article 20 may have the embedded memory 21, and identification information of the article 20 may be stored in the memory 21. In the present disclosure, the "identification information of the article 20" may indicate information on the type of the article 20. For example, the identification information of the article 20 may include information on whether the article 20 is a first article or a second article that is different from the first article. In another example, the identification information of the article 20 may include information on the number of times that the article 20 may be used. For example, when the number of times available is set to 20, the output unit 250 may use a current profile of the inserted article 20 only 20 times.

In addition, although only the embodiment in which the article 20 has a stick shape is illustrated in the drawings, the shape of the article 20 is not limited to the stick shape.

The second processor 230 may be electrically connected to the at least one electrical connection member 260, and when the article 20 is accommodated in or inserted into the accommodation space 210*i*, the second processor 230 may be electrically connected to the memory 21 of the article 20 through the at least one electrical connection member 260. That is, the second processor 230 may be electrically connected to the memory 21 of the article 20 through the at least one connection member 260.

The second processor 230 may receive a signal including identification information of the article 20 from the memory 21 of the article 20 through the at least one electrical connection member 260 and detect the type of the article 20 accommodated in or inserted into the accommodation space 210*i* based on the received signal.

According to one embodiment, the second processor 230 may adjust the intensity of a current applied to a user's body (for example, the body B of FIG. 4) from the output unit 250 based on the type of the detected article 20. In this case, the second processor 230 may adjust the intensity of the current applied to a user's body from the output unit 250 by controlling power supplied from the second battery 240 to the output unit 250 depending on the type of the detected article 20.

In one example, when it is detected that the article 20 accommodated in the accommodation space 210*i* is a first article, the second processor 230 may control the output unit 250 such that brain stimulation corresponding to a first brain stimulation profile is applied to a user. In another example, when it is detected that the article 20 accommodated in the accommodation space 210*i* is a second article that is different from the first article, the second processor 230 may control the output unit 250 such that brain stimulation corresponding to a second brain stimulation profile that is different from the first brain stimulation profile is applied to a user.

In the present disclosure, a "brain stimulation profile" may indicate a change in brain stimulation applied to a user over time. For example, when stimulation corresponding to the first brain stimulation profile is applied to a user, the user may feel a smoking sensation like smoking a cigarette corresponding to the first article. Similarly to this, when stimulation corresponding to the second brain stimulation profile is applied to a user, the user may feel a smoking sensation like smoking a cigarette corresponding to the second article.

The brain stimulation device 200 according to one embodiment may provide different brain stimulation to a user depending on the type of the article 20 accommodated in the accommodation space 210*i*, and thus, various smoking sensations or a stress or tension relief effect may be provided to the user. Accordingly, a user may feel various smoking sensations or reduce stress or tension through brain stimulation applied by the brain stimulation device 200, and thus, the same effect as smoking may be obtained without a separate smoking behavior.

FIG. 6 is a flowchart illustrating operations of a brain stimulation system. In addition, FIG. 7A is a graph illustrating an example of a change in current applied to a user's body when a first article is inserted into a brain stimulation device, and FIG. 7B is a graph illustrating an example of a change in current applied to a user's body when a second article is inserted into a brain stimulation device. In addition, FIG. 8A is a view illustrating that detected biometric information of a user is displayed as a virtual reality image or an augmented reality image, FIG. 8B is a view illustrating that a smoking progress rate is displayed as a virtual reality image or an augmented reality image, and FIG. 8C is a view illustrating that a use stop warning message is displayed as a virtual reality image or an augmented reality image. FIG. 9A is a view illustrating that cigarette smoke is displayed as a virtual reality image or an augmented reality image, and FIGS. 9B and 9C are views illustrating that a natural environment or a certain space for stress relief is displayed as a virtual reality image. FIG. 10 is a view illustrating a sound reproduction device according to one embodiment.

Hereinafter, operations 601, 602, and 603 of applying a current of the brain stimulation device of FIG. 6 are described with reference to components of the brain stimulation device 200 illustrated in FIGS. 3 to 5 and current profiles P1 and P2 illustrated in FIGS. 7A and 7B. Also, operations 604 and 605 of displaying biometric information changed by brain stimulation of FIG. 6 as a virtual reality or augmented reality image are described with reference to components of the wearable electronic device 100 illustrated in FIGS. 1 and 2, virtual reality images or augmented reality images illustrated in FIGS. 8A to 9C, and a sound reproduction device illustrated in FIG. 10.

Referring to FIG. 6, in operation 601, the second processor 230 of the brain stimulation device 200 according to one embodiment may detect the type of the article 20 accommodated in or inserted into the brain stimulation device 200.

According to one embodiment, the second processor 230 may detect the type of the article 20 accommodated in the accommodation space 210i through the at least one electrical connection member 260 electrically connected to the memory 21 of the article 20. For example, the second processor 230 may receive a signal including identification information of the article 20 from the memory 21 of the article 20 through the at least one electrical connection member 260 and may detect the type of the article 20 based on the received signal.

In operation 602, the second processor 230 of the brain stimulation device 200 according to one embodiment may determine a brain stimulation profile to be applied to a user based on the type of the article 20 detected in operation 601.

In one example, when it is detected that a first article is accommodated in the accommodation space 210i, the second processor 230 may determine a first brain stimulation profile corresponding to the first article. In another example, when it is detected that a second article that is different from the first article is accommodated in the accommodation space 210i, the second processor 230 may determine a second brain stimulation profile corresponding to the second article.

Referring to FIGS. 4, 7A, and 7B, in operation 603, the second processor 230 of the brain stimulation device 200 according to one embodiment may apply a current to the user's body B through the output unit 250 such that brain stimulation corresponding to the brain stimulation profile determined in operation 602 is applied to the user.

Referring to FIG. 7A, when it is detected that the first article is accommodated in the accommodation space 210i, the second processor 230 may apply a micro-current corresponding to a first current profile P1 to the user's body B through the output unit 250 such that brain stimulation corresponding to a first brain stimulation profile is applied to the user. In this case, the first current profile P1 may indicate a change in current for providing the brain stimulation corresponding to the first brain stimulation profile to the user.

In other words, when the first article is accommodated in the accommodation space 210i, the second processor 230 may apply a current corresponding to the first current profile P1 to the user's body B through the output unit 250, and as a result, the brain stimulation corresponding to the first brain stimulation profile may occur in the user's brain.

Referring to FIG. 7B, when it is detected that a second article is accommodated in the accommodation space 210i, the second processor 230 may apply a micro-current corresponding to a second current profile P2 to the user's body B through the output unit 250 such that brain stimulation corresponding to a second brain stimulation profile that is different from first brain stimulation profile is applied to the user. In this case, the second current profile P2 may be different from the first current profile P1 and may indicate a change in current for providing the brain stimulation corresponding to the second brain stimulation profile to the user.

In other words, when the second article is accommodated in the accommodation space 210i, the second processor 230 may apply a current corresponding to the second current profile P2 to the user's body B through the output unit 250, and as a result, the brain stimulation corresponding to the second brain stimulation profile that is different from the first brain stimulation profile may occur in the user's brain.

The brain stimulation device 200 according to one embodiment may provide different types of brain stimulation to a user depending on the type of the article 20 accommodated in the accommodation space 210i through operations 601 to 603 described above, and as a result, the user may feel various smoking sensations with only brain stimulation without a separate smoking behavior.

When smoking a general cigarette, a user may easily recognize a smoking effect because side-stream smoke is generated in case of a combustion method, and aerosol is generated in case of a heating method. By contrast, the brain stimulation device 200 according to an embodiment of the present application obtains a smoking effect through only brain wave stimulation, and accordingly, a user may experience difficulty in directly recognizing a smoking effect. Therefore, there is a need to improve the reliability of a smoking effect according to use of the brain stimulation device 200. Hereinafter, a method of increasing the feeling of a smoking effect according to use of the wearable electronic device 100 will be described below with reference to operations 604 and 605.

Referring to FIGS. 1 and 2, in operation 604, the first processor 110 according to one embodiment may detect biometric information of a user changed due to a current applied to the user's body B in operation 603 by using the biometric information acquisition unit 140.

The first processor 110 according to one embodiment may detect (track) the biometric information of the user by using the biometric information acquisition unit 140 from a point in time when a current is applied from the brain stimulation device 200 to the user's body B to a point in time when the application of the current ends. The biometric information acquisition unit 140 may include at least one of the heart rate measurement sensor 141, the body temperature measurement sensor 142, the electrocardiogram measurement sensor 143, the sweat measurement sensor 144, and an oxygen saturation measurement sensor. Hereinafter, for the sake of convenience of description, it is assumed that the biometric information acquisition unit 140 includes the heart rate measurement sensor 141, the body temperature measurement sensor 142, and the electrocardiogram measurement sensor 143.

Referring to FIGS. 1, 2, and 8A, in operation 605, the first processor 110 may display a virtual reality image or an augmented reality image providing biometric information of a user detected in operation 604 on the display 120.

As a user wears the wearable electronic device 100 on a part (for example, the head) of a user's body, the user may view a real surrounding environment BG through the display 120. In this case, the display 120 may correspond to a transparent lens in a state in which separate image data is not output. Therefore, the real surrounding environment BG that a user may see through the display 120 may indicate a surrounding environment in a real space where the user uses the brain stimulation device 200.

The first processor 110 according to one embodiment may display the user's biometric information (for example, a heart rate, an electrocardiogram interval, and body temperature) on the display 120 in real time when a current is applied from the brain stimulation device 200 to the user's body B. The user's biometric information may be displayed as a virtual reality image or an augmented reality image. FIG. 8A illustrates an embodiment in which the user's biometric information is displayed as an augmented reality image IMG1.

Due to this, the user may intuitively experience a smoke effect according to brain stimulation by checking biometric information that changes in real time.

Referring to FIG. 8B, the first processor 110 according to one embodiment may calculate a smoking progress rate based on a brain stimulation profile (see FIGS. 7A and 7B) of the article 20 and display a virtual reality image or an augmented reality image providing the smoking progress rate on the display 120. FIG. 8B illustrates an embodiment in which the smoking progress rate is displayed as an augmented reality image IMG2. For example, the first processor 230 may determine the smoking progress rate in proportion to a progress time of a current profile. In this case, the total progress time of the current profile may be set within a preset range (for example, 1 minute to 3 minutes).

Alternatively, the first processor 230 according to one embodiment may calculate the smoking progress rate based on a change in biometric information of a user and display a virtual reality image or an augmented reality image providing the smoking progress rate on the display 120. For example, the first processor 230 may determine the smoking progress rate in proportion to the degree to which a heart rate reaches a preset value, determine the smoking progress rate in proportion to the degree to which the body temperature reaches a preset value, or determine the smoking progress rate in proportion to the degree to which an electrocardiogram interval reaches a preset value. In this case, the preset values may be set by measuring in advance a heart rate, body temperature, and an electrocardiogram interval of a user at a point in time when the brain stimulation according to a current profile of the article 20 ends. However, the method of determining the smoking progress rate is not limited thereto. For example, the smoking progress rate may be determined by comprehensively considering the electrocardiogram interval, the body temperature, and the heart rate.

Even before the progression of the current profile of the article 20 is completed, if the calculated smoking progress rate reaches 100%, the first processor 230 may display, on the display 120, a message asking to confirm stopping the operation of the brain stimulation device 200.

Referring to FIG. 8C, when biometric information (for example, a heart rate, an electrocardiogram interval, and body temperature) is out of a preset threshold, the first processor 110 according to one embodiment may display, on the display 120, a virtual reality image or an augmented reality image providing a warning message to stop using the brain stimulation device 200. FIG. 8C illustrates an embodiment in which a warning message is displayed as an augmented reality image IMG3. In this case, the preset threshold may be set to a value considered to be likely to cause harm to the health of a user through clinical trials.

For example, when an electrocardiogram interval is reduced to a first threshold or less, when the body temperature increases to the first threshold or more, or when a heart rate increases to the first threshold or more, the first processor 110 may display a warning message on the display 120. Alternatively, when two or more of these items are applicable, the first processor 110 may display a warning message on the display 120.

Even before progress of a current profile of the article 20 is completed, when biometric information (for example, a heart rate, an electrocardiogram interval, and body temperature) exceeds a preset threshold, the first processor 230 according to one exemplary embodiment may immediately stop operation of the brain stimulation device 200.

Referring to FIGS. 7A, 7B, and 9A, the first processor 110 according to one embodiment may display an image of virtual reality or augmented reality in which cigarette smoke is generated and may control the display 120 to change the image of at least one of a color, an amount, and a shape of the cigarette smoke, based on the brain stimulation profile of the article 20.

The first processor 110 may output a virtual reality image or an augmented reality image corresponding to a smoking event through the display 120. In one embodiment, the virtual reality image or the augmented reality image displayed on the display 120 may be set based on the type (or the brain stimulation profile) of the article 20.

The first processor 110 may determine image data corresponding to the first brain stimulation profile. For example, the electronic device 100 may determine image data corresponding to the first brain stimulation profile based on data previously stored in the memory 21 of FIG. 5. In this case, the memory may store the image data corresponding to the first brain stimulation profile in advance. Thereafter, the first processor 110 may display an augmented reality image IMG4 corresponding to the determined first brain stimulation profile on the display 120. For example, a user may see, through the display 120, a screen in which the augmented reality image IMG4 including cigarette smoke corresponding to the first brain stimulation profile overlaps the actual surrounding environment BG.

The first processor 110 may determine image data corresponding to the second brain stimulation profile. For example, the electronic device 100 may determine the image data corresponding to the second brain stimulation profile based on data previously stored in the memory 21 of FIG. 5. In this case, the memory may store image data corresponding to the second brain stimulation profile in advance. Thereafter, the first processor 110 may display an augmented reality image IMG5 corresponding to the determined second brain stimulation profile on the display 120. For example, a user may see, through the display 120, a screen in which the augmented reality image IMG5 including cigarette smoke corresponding to the second brain stimulation profile overlaps the actual surrounding environment BG.

The augmented reality image IMG4 corresponding to the first brain stimulation profile may include an object having a different shape from an object included in the augmented reality image IMG5 corresponding to the second brain stimulation profile. For example, the augmented reality image IMG4 corresponding to the first brain stimulation profile and the augmented reality image IMG5 corresponding to the second brain stimulation profile may include an image of cigarette smoke, and the shapes of cigarette smoke (for example, the amount and/or form of cigarette smoke) and/or colors of the cigarette smoke may be different from each other.

That is, when a user selects a first article in which the first brain stimulation profile is stored, the augmented reality image IMG4 corresponding to the first brain stimulation profile set to have a small amount of haze may be displayed on the display 120, and when the user selects a second article in which the second brain stimulation profile is stored, the augmented reality image IMG5 corresponding to the second brain stimulation profile set to have a large amount of haze may be displayed on the display 120.

For example, although not illustrated in the drawings, when a brain stimulation profile is designed to include grape flavor, cigarette smoke may be changed to purple.

Referring to FIGS. 1, 9B, and 9C, when biometric information (for example, a heart rate, an electrocardiogram interval, and body temperature) corresponds to a preset stress range, the first processor 110 according to one embodiment may display a preset virtual reality image or an augmented reality image for relieving stress on the display 120.

The virtual reality image or the augmented reality image for stress relief may include an image of a natural environment (see FIG. 9B) or a certain place (see FIG. 9C) that relieves stress of a user. FIG. 9B illustrates an embodiment in which a forest is displayed as a virtual reality image IMG6. FIG. 9C illustrates an embodiment in which a living room is displayed as a virtual reality image IMG7. In this case, the virtual reality images IMG6 and IMG7 may be still images or moving images.

However, an image of the forest or the living room is an example, and the virtual reality image or the augmented reality image for stress relief may include any other images (for example, a celebrity, an animal, or so on) for each type of the article 20. The virtual reality image or the augmented reality image for stress relief may be stored in the memory 21.

The first processor 110 may determine whether there is stress based on whether a heart rate, an electrocardiogram interval, and body temperature are within a preset stress range. For example, when the heart rate increases to be within a preset stress range, when the electrocardiogram interval decreases to be within a preset stress range, or when the body temperature increases to be within a preset stress range, the first processor 110 may determine that a stress index of a user is increased. Alternatively, when two or more of these items are applicable, the first processor 110 may determine that the stress index of the user is increased.

Referring to FIGS. 9B, 9C, and 10, the brain stimulation system 1 may further include a sound reproduction device. Earphones ER are illustrated as an example of the sound reproduction device. When a user wears the earphones ER, ear tips ET of the earphones ER may be inserted into the ears of the user. A jack EJ of the earphones ER may be connected to the wearable electronic device 100 of FIG. 1. However, examples of the sound reproduction device are not limited to the earphones EP illustrated in FIG. 10 and may include headphones, a bone conduction speaker, and so on. In addition, although the earphones EP of FIG. 10 are illustrated as a wire, the earphones are not limited thereto and may be wireless.

The first processor 110 of FIG. 2 may output a sound corresponding to the virtual reality image or the augmented reality image for stress relief through a sound reproduction device. For example, when the forest image of FIG. 9B is displayed on the display 120 of FIG. 1 as a virtual reality or an augmented reality image for stress relief, the earphones ER may output a sound of a chirping bird, a sound of a flowing stream, or so on. When the living room image of FIG. 9C is displayed on the display 120 of FIG. 1 as the virtual reality or the augmented reality image for stress relief, the earphones ER may output jazz music, classical music, or so on.

A sound source corresponding to a virtual reality image or an augmented reality image for stress relief may be stored in the memory 21 of the article 20.

FIG. 11 is a perspective view illustrating a brain stimulation device according to another embodiment.

Referring to FIG. 11, a brain stimulation device 1000 according to one embodiment may include a brain stimulation device module 200' attached to a user's body B and a control module 300 for controlling the brain stimulation device module 200'. A connection between the wearable electronic device 100 of FIG. 1 and the brain stimulation device 1000 is substantially the same as the configuration described with reference to FIGS. 1 to 10, and accordingly, redundant descriptions thereof are omitted, and a connection between the brain stimulation device module 200' and the control module 300 will be mainly described.

The brain stimulation device module 200' may be attached to at least one area of the user's body B and apply a micro-current to provide brain stimulation corresponding to a smoking sensation to a user.

According to one embodiment, the brain stimulation device module 200' may include a first housing 210' and an output unit (not illustrated) (for example, the output unit 250 of FIG. 4).

The first housing 210' may form the entire appearance of the brain stimulation device module 200', and an internal space (or a 'mounting space') in which components of the brain stimulation device module 200' may be arranged may be formed inside the first housing 210'. For example, a processor (for example, the second processor 230 of FIG. 4), a battery (for example, the second battery 240 of FIG. 4), and the output unit may be in the inner space of the first housing 210' and are not limited thereto.

Although the drawing illustrates only the embodiment in which the first housing 210' has a shape of a rectangular patch as a whole, the shape of the first housing 210' is not limited thereto. In another example, the first housing 210' may have a shape of an elliptical patch or a polygonal patch.

The output unit may provide brain stimulation to the user by applying a current to the user's body B based on the supplied power. For example, the output unit may apply a current to the user's body B through at least one area of the first housing 210' that comes into contact with the user's body B.

The control module 300 may be operatively connected to the brain stimulation device module 200' to control all operations of the brain stimulation device module 200'. That is, a user may adjust a power state of the brain stimulation device module 200' and/or the intensity and so on of a current applied to the user's body B from the brain stimulation device module 200' through the control module 300.

According to one embodiment, the control module 300 may include a second housing 310 including an accommodation space 310i which an article 20 may be accommodated in or inserted into, and at least one button portion 320 receiving a user input.

The second housing 310 may form the entire appearance of the control module 300, and the accommodation space 310i which at least a part of the article 20 may be accommodated in or inserted into may be in one area of the second housing 310. The control module 300 may detect the type of the article 20 accommodated in or inserted into the accommodation space 310i of the second housing 310 and transmit data corresponding to the type of the detected article 20 to the brain stimulation device module 200'. The brain stimulation device module 200' may control the intensity or a frequency of the current applied to the user's body B based on the data on the type of the article 20 received from the control module 300.

Although FIG. 11 illustrates only an embodiment in which the second housing 310 has a cylindrical shape as a whole, the shape of the second housing 310 is not limited thereto. According to the embodiment, the second housing 310 may be formed as a polygonal pillar (for example, a quadrangular or pentagonal pillar).

The at least one button portion 320 may be on an outer surface of the second housing 310 to receive a user input. A processor (not illustrated) of the control module 300 may transmit a signal for controlling an operation of the brain stimulation device module 200' to the brain stimulation device module 200' based on the user input to the at least one button portion 320.

According to one embodiment, the at least one button portion 320 may include a first button portion 321 for controlling a power state of the brain stimulation device module 200' and a second button portion 322 for controlling the intensity of brain stimulation or a current applied to a user from the brain stimulation device module 200'. However, the number of at least one button portion 320 is not limited to the embodiment described above, and the number of button portions may increase or decrease depending on embodiments.

In one example, when receiving a user input to the first button portion 321, the processor of the control module 300 may transmit a signal including data for controlling the power state of the brain stimulation device module 200' to the brain stimulation device module 200'. Based on the signal received from the control module 300, the brain stimulation device module 200' may switch the power state from an on-state to an off-state, and vice versa.

In another example, when receiving the user input to the second button portion 322, the processor of the control module 300 may transmit a signal including data for controlling the intensity of a current applied to a user to the brain stimulation device module 200'. For example, the brain stimulation device module 200' may control the intensity of the current applied to the user such that strong brain stimulation is applied to the user or brain stimulation is applied more quickly, based on the signal received from the control module 300. In addition, the brain stimulation device module 200' may also control the intensity of the current applied to the user such that weaker brain stimulation is applied to the user or brain stimulation is applied more slowly, based on the signal received from the control module 300.

According to one embodiment, the brain stimulation device 1000 may further include a connector 400 for electrically or operatively connecting the brain stimulation device module 200' to the control module 300.

For example, one end 410 of the connector 400 may be connected to a first electrode 270' of the brain stimulation device module 200', and the other end 420 of the connector 400 may be connected to a second electrode 370 of the control module 300. In this case, the first electrode 270' may be in one area of the first housing 210' of the brain stimulation device module 200', and may electrically connect the connector 400 to the processor of the brain stimulation device module 200'. In addition, the second electrode 370 may be in one area of the second housing 310 of the control module 300 and electrically connect the connector 400 to the processor of the control module 300.

The connector 400 may be composed of, for example, a wire or a flexible printed circuit board (FPCB) but is not limited thereto. As another example, the connector 400 may be composed of an optical axis cable.

The brain stimulation device module 200' may be electrically or operatively connected to the control module 300 through the connector 400 described above, and a signal may be transmitted between the brain stimulation device module 200' and the control module 300 through the connector 400.

According to another embodiment, the brain stimulation device module 200' may be connected wirelessly to the brain stimulation device module 200' without a separate component (for example, the connector 400) connecting the brain stimulation device module 200' to the control module 300. For example, the brain stimulation device module 200' may include a first communication unit for communicating with the control module 300, and the control module 300 may include a second communication unit for communicating with the brain stimulation device module 200'. The brain stimulation device module 200' may be electrically or operatively connected to the control module 300 through the first communication unit and the second communication unit, and as a result, a signal may be transmitted between the brain stimulation device module 200' and the control module 300.

FIG. 12 illustrates a schematic view of a brain stimulation device according to one embodiment. FIG. 13 is a perspective view illustrating the brain stimulation device illustrated in FIG. 12 and an external electronic device.

Referring to FIG. 12, a brain stimulation device 100' illustrated in FIG. 12 has a configuration in which the functions of the brain stimulation device 200 and the wearable electronic device 100 illustrated in FIG. 1 are integrated, and operates in substantially the same manner as the brain stimulation system 1 described with reference to FIGS. 1 to 10.

The brain stimulation device 100' according to one embodiment may include a face plate 101 and a mounting portion 103. The brain stimulation device 100' may include a display 120 on the face plate 101 and include a processor 110', a communication unit 130, a biometric information acquisition unit 140, and a battery 150' which are provided in the mounting portion 103. In this case, the battery 150' may supply power used for the operation of the brain stimulation device 100'. In one example, the battery 150' may supply power required to operate the processor 110'. In another example, the battery 150' may supply power required for the output unit 170 to apply a current to a user's body.

In addition, the brain stimulation device 100' may include an accommodation space 160 in which the article 20 is accommodated, an output unit 170 that has at least one area attached to the user's body and applies a current corresponding to the article 20 to the user's body to apply brain stimulation to the user such that the user may feel a smoking sensation, and a button portion 180 including a first button portion 181 for controlling external power and a second button portion 182 for controlling the intensity of a current.

In one embodiment, the processor 110', the communication unit 130, the biometric information acquisition unit 140, the battery 150', the accommodation space 160, the output unit 170, and the button portion 180 may be in at least a portion of the mounting portion 103 of the wearable electronic device 100', and the portion where the respective components are arranged is not limited thereto. However, the biometric information acquisition unit 140 and the output unit 170 have to be in contact with at least a part of the user's body.

When it is detected that a first article is accommodated in the accommodation space 160, the processor 110' may apply a current corresponding to a first current profile to the user's body through the output unit 170 such that brain stimulation corresponding to the first brain stimulation profile is applied to the user, and when it is detected that a second article that is different from the first article is accommodated in the accommodation space 160, the processor 110' may apply a current corresponding to a second current profile to the user's body through the output unit 170 such that brain stimulation corresponding to the second brain stimulation profile is applied to the user.

The biometric information acquisition unit 140 may detect the changed biometric information of a user in response to the brain stimulation of the output unit 170. The biometric information acquisition unit 140 may include at least one of the heart rate measurement sensor 141 of FIG. 2, the body temperature measurement sensor 142 of FIG. 2, the electrocardiogram measurement sensor 143 of FIG. 2, the sweat measurement sensor 144 of FIG. 2, and an oxygen saturation measurement sensor.

The processor 110' may display, on the display 120, a virtual reality image or an augmented reality image IMG1 of FIG. 8A providing the detected biometric information of a user.

The processor 110' may display a virtual reality image or an augmented reality image IMG2 of FIG. 8A providing a smoking progress rate on the display 120 in response to a change in biometric information.

When the biometric information is greater than or equal to a preset threshold, the processor 110' may display, on the display 120, a virtual reality image or an augmented reality image providing a warning message to stop using the brain stimulation device 100'.

The processor 110' may display a virtual reality image or an augmented reality image IMG4 or IMG5 of FIG. 9A in which cigarette smoke is generated and may control the display 120 to change the image of at least one of a color, an amount, and a shape of the cigarette smoke depending on the type of the article 20.

When the biometric information corresponds to a preset stress range, the processor 110' may display a preset virtual reality image or a preset augmented reality image for stress relief on the display 120. The virtual reality image or the augmented reality image for stress relief may include a natural environment image IMG6 of FIG. 9B and a certain space image IMG7 of FIG. 9B for stress relief of a user.

The brain stimulation device 100' may further include the sound reproduction device ER of FIG. 10, and the processor 100' may output a sound corresponding to the virtual reality image or the augmented reality images IMG6 and IMG7 of FIG. 9B for stress relief through the sound reproduction device ER.

Referring to FIG. 13, the brain stimulation device 100' may be connected to an external device 500 through the communication unit 130 by wire and/or wirelessly. Accordingly, the brain stimulation device 100' may transmit a signal to the external device 500 through the communication unit 130 or receive a signal from the external device 500 through the communication unit 130.

The communication unit 130 may include at least one component for communication between the brain stimulation device 100' and the external device 500. For example, the communication unit 130 may include a short-range wireless communication unit and a wireless communication unit.

Although FIG. 13 illustrates only an embodiment in which the brain stimulation device 100' is wirelessly connected to the external device 500 in the form of a mobile electronic device, the embodiment is not limited thereto. Depending on embodiments, the brain stimulation device 100' may be connected to the external device 500 by wire or may be connected to other electronic devices other than a mobile electronic device.

The processor 110' of the brain stimulation device 100' according to one embodiment may control all operations of the brain stimulation device 100' based on a signal received by wire or wirelessly from the external device 500. A signal received from the external device 500 may include data for controlling the operation of the brain stimulation device

100', and the processor 110' may control the operation of the brain stimulation device 100' based on data included in the received signal.

In one example, the processor 110' of the brain stimulation device 100' may switch the power of the brain stimulation device 100' from an on-state to an off-state, and vice versa based on the signal received from the external device 500.

In another example, the processor 110' of the brain stimulation device 100' may determine the intensity of a current applied to a user from the output unit 170 of the brain stimulation device 100' based on the signal received from the external device 500.

That is, the processor 110' illustrated in FIG. 13 may control all operations of the brain stimulation device 100' based on not only a user input to the at least one button portion 180 but also a user input to the external device 500. Accordingly, a user may control the brain stimulation device 100' in various ways, and thus, usability of the brain stimulation device 100' may be improved.

Operations of a brain stimulation device or a brain stimulation system according to various embodiments of the present disclosure may be implemented in the form of a recording medium including instructions executable by a computer, such as a program module that is executed by the computer. A computer-readable medium may be any available medium that is accessible by a computer and include all of volatile and nonvolatile media and removable and non-removable media. In addition, the computer-readable medium may include both a computer storage medium and a communication medium. The computer storage medium may include all of volatile and nonvolatile media and removable and non-removable media implemented by any method or technology for storage of information, such as computer-readable instructions, data structures, program modules, or other data. The communication medium typically includes computer-readable instructions, data structures, other data of a modulated data signal such as program modules, or other transport mechanism, and includes any information transmission media.

Those of ordinary skill in the art related to the present embodiments may understand that various changes in form and details can be made therein without departing from the scope of the characteristics described above. Therefore, the disclosed methods should be considered in a descriptive point of view, not a restrictive point of view. The scope of the present disclosure is defined by the appended claims rather than by the foregoing description, and all differences within the scope of equivalents thereof should be construed as being included in the present disclosure.

The invention claimed is:

1. A brain stimulation system comprising:
a wearable electronic device including a display, a biometric information acquisition unit, and a first processor; and
a brain stimulation device having at least one area configured to be attached to a body of a user and apply brain stimulation to the user such that the user feels a smoking sensation, the brain stimulation corresponding to brain waves changed by smoking,
wherein the biometric information acquisition unit detects biometric information of the user that changes in response to the brain stimulation, and
the first processor controls the display to display one of a virtual reality image and an augmented reality image including the detected biometric information of the user.

2. The brain stimulation system of claim 1, wherein the biometric information acquisition unit includes at least one of a heart rate measurement sensor, an electrocardiogram measurement sensor, a body temperature measurement sensor, a sweat measurement sensor, and an oxygen saturation measurement sensor.

3. The brain stimulation system of claim 1, wherein the first processor controls the display to display one of a virtual reality image and an augmented reality image including a smoking progress rate based on a change in the biometric information.

4. The brain stimulation system of claim 1, wherein first processor controls the display to display a virtual reality image or an augmented reality image including a warning message to stop using the brain stimulation device when the biometric information is greater than or equal to a preset threshold.

5. The brain stimulation system of claim 1, wherein the brain stimulation device comprises:

a housing including an accommodation space for accommodating an article;

an output unit configured to out a current; and a second processor configured to control the output unit to provide a current corresponding to the article to the body of the user.

6. The brain stimulation system of claim 5, wherein the article is a cigarette-shaped memory stick including a memory in which identification information is stored.

7. The brain stimulation system of claim 6, wherein identification information includes a type of the article and a number of available uses of the article.

8. The brain stimulation system of claim 5, wherein the second processor applies a current corresponding to a first current profile to the body of the user through the output unit such that brain stimulation corresponding to a first brain stimulation profile is applied to the user when it is detected that a first article is accommodated in the accommodation space, and the second processor applies a current corresponding to a second current profile to the body of the user through the output unit such that brain stimulation corresponding to a second brain stimulation profile is applied to the user when it is detected that a second article different from the first article is accommodated in the accommodation space.

9. The brain stimulation system of claim 8, wherein the first processor displays one of a virtual reality image and an augmented reality image in which cigarette smoke is generated, and controls the display to change an image of at least one of a color, an amount, and a shape of the cigarette smoke depending on a type of the article.

10. The brain stimulation system of claim 8, wherein the first processor displays one of a preset virtual reality image for stress relief and a preset augmented reality image for stress relief on the display when the biometric information corresponds to a preset stress range.

11. The brain stimulation system of claim 10, wherein the one of the preset virtual reality image for stress relief and the preset augmented reality image for stress relief includes an image of a natural environment or a certain place selected for stress relief of the user.

12. The brain stimulation system of claim 11, further comprising a sound reproduction device, wherein the first processor controls the sound reproduction device to output a sound corresponding to the one of the preset virtual reality image for stress relief and the preset augmented reality image for stress relief.

13. The brain stimulation system of claim 1, wherein the wearable electronic device includes a first communication unit, and the brain stimulation device includes a second communication unit for communicating with the first communication unit.

14. A brain stimulation device comprising:

a display;

a biometric information acquisition unit;

an accommodation space configured to accommodate an article;

an output unit having at least one area configured to be attached to a body of a user and apply a current corresponding to the article to the body of the user to apply brain stimulation to the user such that the user feels a smoking sensation, the brain stimulation corresponding to brain waves changed by smoking; and a processor configured to control operations of the display, the biometric information acquisition unit, and the output unit, wherein the biometric information acquisition unit detects biometric information of the user that changes in response to the brain stimulation, and the processor controls the display to display one of a virtual reality image and an augmented reality image including the detected biometric information of the user.

15. The brain stimulation device of claim 14, wherein the biometric information acquisition unit includes at least one of a heart rate measurement sensor, an electrocardiogram measurement sensor, a body temperature measurement sensor, a sweat measurement sensor, and an oxygen saturation measurement sensor.

* * * * *